US012042441B2

(12) United States Patent
Turocy et al.

(10) Patent No.: US 12,042,441 B2
(45) Date of Patent: Jul. 23, 2024

(54) INTEGRATED PATIENT SUPPORT AND EQUIPMENT FOR MEDICAL PROCEDURES

(71) Applicant: Reliance Medical Products, Mason, OH (US)

(72) Inventors: Erik M. Turocy, Gahanna, OH (US); Terry M. Birchler, Gahanna, OH (US); Jeffrey D. Accursi, Gahanna, OH (US); Sarvesh S. Chakradeo, Gahanna, OH (US); Brad J. Bocook, Gahanna, OH (US)

(73) Assignee: Reliance Medical Products, Mason, OH (US)

( * ) Notice: Subject to any disclaimer, the term of this patent is extended or adjusted under 35 U.S.C. 154(b) by 614 days.

(21) Appl. No.: 17/287,679

(22) PCT Filed: Oct. 25, 2019

(86) PCT No.: PCT/US2019/058059
§ 371 (c)(1),
(2) Date: Apr. 22, 2021

(87) PCT Pub. No.: WO2020/086960
PCT Pub. Date: Apr. 30, 2020

(65) Prior Publication Data
US 2021/0369530 A1 Dec. 2, 2021

Related U.S. Application Data

(60) Provisional application No. 62/750,769, filed on Oct. 25, 2018.

(51) Int. Cl.
*A61G 15/10* (2006.01)
*A61B 3/00* (2006.01)
(Continued)

(52) U.S. Cl.
CPC ............ *A61G 15/10* (2013.01); *A61B 3/0083* (2013.01); *A61B 90/35* (2016.02); *A61B 90/50* (2016.02); *A61G 15/12* (2013.01); *A61G 2203/12* (2013.01)

(58) Field of Classification Search
CPC ........ A61G 15/02; A61G 15/10; A61G 15/12; A61G 2203/12; A61B 3/0083; A61B 90/35; A61B 90/50
(Continued)

(56) References Cited

U.S. PATENT DOCUMENTS 3,572,913 A * 3/1971 Korb ........................ A61B 3/18
250/221
4,741,506 A * 5/1988 Schwaegerle .......... A61G 15/10
297/344.1
(Continued)

*Primary Examiner* — William R Alexander
(74) *Attorney, Agent, or Firm* — TAFT STETTINIUS & HOLLISTER LLP; Derek B. Lavender; Ryan O. White

(57) ABSTRACT

An integrated medical equipment for supporting medical equipment and a patient during a medical procedure. The integrated medical equipment includes a base, an adjustable chair operatively connected to the base, and an equipment support operatively connected to the base and spaced from the adjustable chair by a predetermined distance. The equipment support includes a column at the base and a tower extending generally vertically from the column. A medical device arm is operatively connected to the tower, wherein the medical device arm is motor driven to move along the generally vertical tower. A platform support arm is operatively connected to the column, wherein the platform support arm is motor driven to move generally vertically along the column.

19 Claims, 17 Drawing Sheets

(51) Int. Cl.
*A61B 90/35* (2016.01)
*A61B 90/50* (2016.01)
*A61G 15/12* (2006.01)

(58) Field of Classification Search
USPC .......................................................... 351/200
See application file for complete search history.

(56) References Cited

U.S. PATENT DOCUMENTS

| | | | | |
|---|---|---|---|---|
| 4,790,647 | A * | 12/1988 | Mann | G05B 19/23 |
| | | | | 351/245 |
| 10,335,339 | B1 * | 7/2019 | Stees | A61G 15/10 |
| 2002/0163624 | A1 * | 11/2002 | O'Brien | A61B 3/0033 |
| | | | | 351/245 |
| 2004/0218142 | A1 * | 11/2004 | Wakil | A61B 3/0091 |
| | | | | 351/205 |
| 2007/0109498 | A1 * | 5/2007 | Lai | A61B 3/1015 |
| | | | | 351/206 |
| 2009/0027619 | A1 * | 1/2009 | Kendrick | A61B 3/0083 |
| | | | | 351/245 |
| 2013/0100411 | A1 * | 4/2013 | Corrigan | A61B 3/0083 |
| | | | | 351/245 |
| 2013/0100412 | A1 * | 4/2013 | Schwaegerle | A61B 3/0083 |
| | | | | 351/245 |
| 2013/0293845 | A1 * | 11/2013 | Kendrick | A61B 90/50 |
| | | | | 351/214 |
| 2016/0324415 | A1 * | 11/2016 | Schwaegerle | A61B 3/0075 |
| 2019/0029514 | A1 * | 1/2019 | Tsukada | A61B 3/0025 |

\* cited by examiner

INTEGRATED PATIENT SUPPORT AND EQUIPMENT FOR MEDICAL PROCEDURES

CROSS-REFERENCE TO RELATED APPLICATION

This application claims priority to U.S. Provisional Application No. 62/750,769, filed Oct. 25, 2018 entitled "Integrated Patient Support and Equipment for Medical Procedures", the disclosure of which is hereby incorporated by reference in its entirety.

TECHNICAL FIELD

The present disclosure is generally related to medical equipment for performing medical procedures and more particularly to an integrated patient support and equipment for performing medical procedures for the eye.

BACKGROUND

Lift and recline chairs of the type used, for example, during medical, dental and optical examinations and procedures are known in the prior art. Many times, these chairs are power operated by electric motors or hydraulic motors and may be moved vertically with respect to a base and/or reclined to place the patient in a recumbent or supine position. The chair is moved by the operator, i.e., the doctor, dentist or other medical professional, by way of a plurality of switches which may be attached to the chair itself or made part of a separate switch panel or foot switch assembly. Although various improvements have been made over the years for such powered adjustable chairs and associated equipment, certain problems and undesirable aspects associated with past designs have become apparent.

The patient support for performing an optical examination is typically a patient support chair that is moved vertically (up and down) and in an upright to a tilted position by the medical professional. The patient support chair is located near a structure that supports one or more medical instruments such as a phoropter and a slit lamp used to execute the medical examination. In a typical procedure, the medical professional moves the medical instruments to a seated patient. The medical instruments, however, cannot always be appropriately positioned to the patient to perform the procedure due the differences in patient types. Consequently, even when the medical professional adjusts the equipment to the patient, the patient must still adjust his or her position to the medical instrument for the procedure.

The location of the patient support chair must be appropriately positioned with respect to medical equipment. Such positioning, however, does not accommodate all patients, and the medical professional must often move to an uncomfortable position to complete the medical procedure. What is needed, therefore, is integrated patient support and equipment for performing medical procedures to improve patient positioning with respect to the medical equipment, medical professional positioning with respect to the medical equipment, and positioning of the medical professional to the patient to improve the performance of medical procedures and consequently patient outcomes.

SUMMARY

The present invention generally relates to integrated medical equipment for performing a medical procedure involving a patient and a medical professional. The integrated medical equipment includes a patient support and an equipment support structure configured to provide an interactive environment where the patient and a medical professional are directed along lanes of movement to interface the patient and the medical professional with the medical equipment. The patient lane and the medical professional lane meet at locations determined by the configuration of the integrated medical equipment such that a medical procedure is performed with accuracy and optimum results for a wide variety of different patient types and different medical professional types. Medical procedure and observation equipment (collectively identified as "procedure equipment") is supported by the integrated medical equipment to be positioned by the medical professional for interaction with the patient. Various procedure equipment supports are configured to direct the procedure equipment to a plurality of adjustable positions. In different embodiments, the procedure supports include limits that prevent the procedure equipment from moving to non-productive locations.

In one embodiment, there is provided an integrated medical equipment for supporting medical equipment and a patient during a medical procedure. The integrated medical equipment includes a base, an adjustable chair operatively connected to the base, and an equipment support operatively connected to the base and spaced from the adjustable chair by a predetermined distance. The equipment support includes a column at the base and a tower extending generally vertically from the column. A medical device arm is operatively connected to the tower, wherein the medical device arm is motor driven to move along the generally vertical tower. A platform support arm is operatively connected to the column, wherein the platform support arm is motor driven to move generally vertically along the column.

In another embodiment, there is provided an integrated medical equipment for supporting medical equipment and a patient during a medical procedure. The integrated medical equipment includes a base, a chair operatively connected to the base, wherein the chair includes an adjustable pedestal to raise and lower the chair. An equipment support is operatively connected to the base and is spaced from the adjustable chair by a predetermined distance. The equipment support includes a column at the base and a tower extending generally vertically from the column. A medical device arm is operatively connected to the tower, wherein the medical device arm is motor driven to move along the generally vertical tower to support a phoropter. A platform support arm is operatively connected to the column, wherein the platform support is motor driven to move generally vertically along the column to support a slit lamp. A monitor is supported by the column. A hand held remote controller is operatively connected to the chair, the medical device arm, the phoropter, the slit lamp, and the monitor. The remote controller controls a position of the chair, a position of the medical device arm, and operation of the phoropter, the slit lamp, and the monitor.

BRIEF DESCRIPTION OF THE DRAWINGS

The above-mentioned aspects of the present invention and the manner of obtaining them will become more apparent and the invention itself will be better understood by reference to the following description of the embodiments of the invention, taken in conjunction with the accompanying drawings, wherein.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

In this regard, the invention is illustrated in the several figures, and is of sufficient complexity that the many parts, interrelationships, and sub-combinations thereof simply cannot be clearly or meaningfully illustrated in a single patent-type drawing. Accordingly, several of the drawings show in schematic, or omit, parts that are not essential in that drawing to a description of a particular feature, aspect or principle of the invention being disclosed. Thus, the best mode of one embodied feature may be shown in one drawing, and the best mode of another feature will be called out in another drawing.

Figure 1:
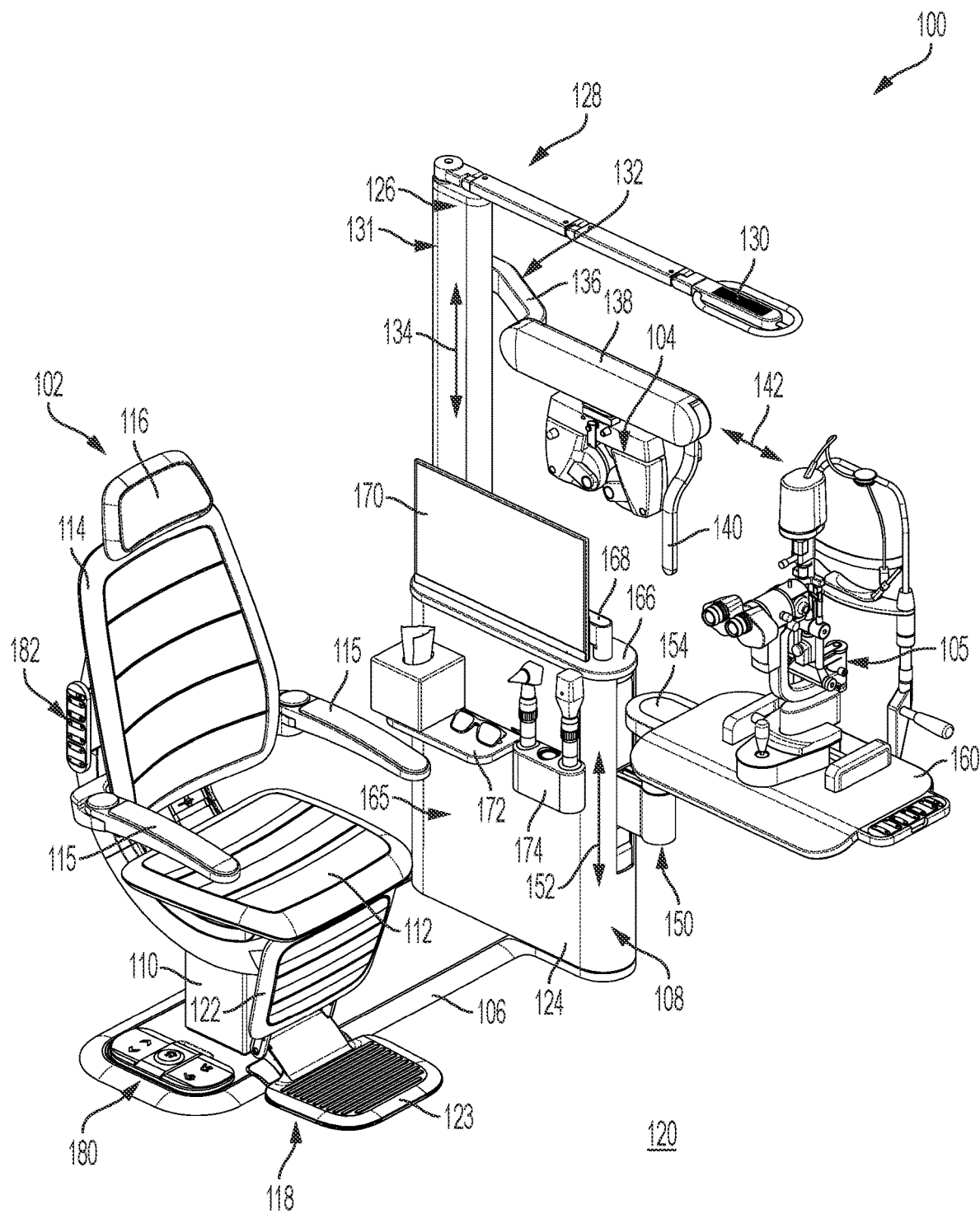
FIG. 1 is a front perspective view of integrated medical equipment including a patient support and procedure equipment supported by a procedure equipment support.

FIG. 1 illustrates a front perspective view of integrated medical equipment 100 including a patient support or patient chair 102 and a procedure equipment support 108, including support of a phoropter 104 and a slit lamp 105. The integrated medical equipment 100 includes a base 106 upon which the patient support 108 is located. The chair 102 is fixedly connected to the base 106 and consequently the distance between the chair 102 and the equipment support 108 is fixed as well.

The chair 102 includes a pedestal 110 fixedly coupled the base 106 and a seat 112 supported by the pedestal 110. In one or more embodiments, pedestal 110 is configured to extend and to retract from the base 106 to raise and lower the chair 102. A back 114 extends from a back portion of the seat 112 and includes a headrest 116 configured to support a patient's head. First and second armrests 115 extend from the back 114 to provide arm support for a patient. A leg rest 118 extends from a front portion of the seat 112 toward a floor 120. The leg rest 118 includes a calf support 122 extending from the seat 112 and a footrest 123 extending from the calf support 122.

The equipment support 108, which extends generally vertically from the floor 120 at one end of the base 106, includes a column 124 configured to provide support for a tower 126 extending generally vertically from the column 124. The tower 126 includes a terminating end configured to rotatably support a first end of an illumination arm 128. A second end of the illumination arm 128 is configured to support an examination light 130. A light source 131 extends along at least a portion of the length of the tower 126 to provide ambient light for the room where the integrated medical equipment is located.

The tower 126 further supports a medical device arm 132 which, in one embodiment, is configured to support the phoropter 104. The medical device arm 132, which is configured to move longitudinally along the tower 126 in the direction 134, includes a first arm 136 and a second arm 138 extending from the first arm 136. The second arm 138 is configured to support the phoropter 104 in a downwardly extending position. A handle 140 is coupled to the second arm 138 to move the phoropter 104 toward and away from the tower 126 along a direction 142.

Figure 2:
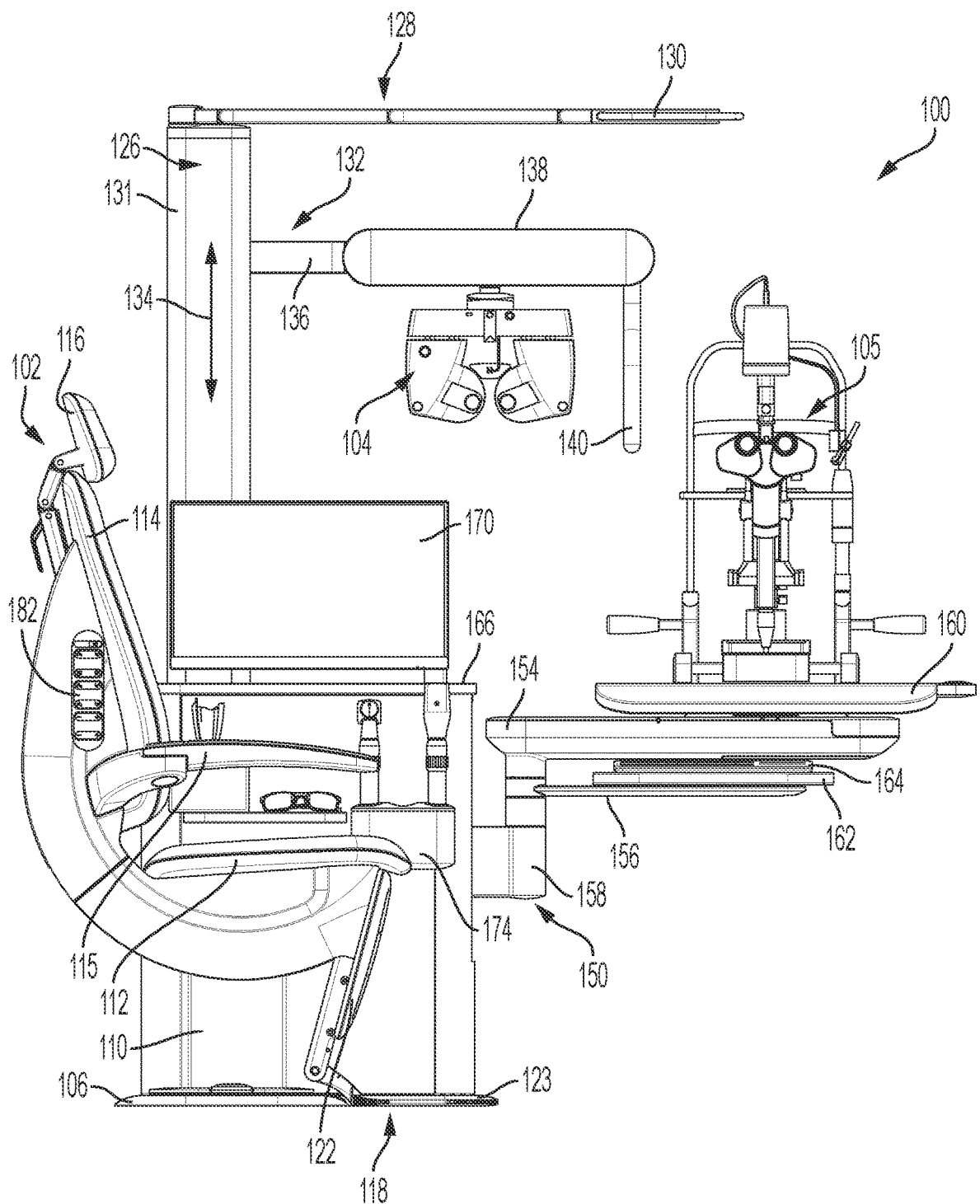
FIG. 2 is a first side elevational view of integrated medical equipment including a patient support and procedure equipment supported by a procedure equipment support.
Figure 3:
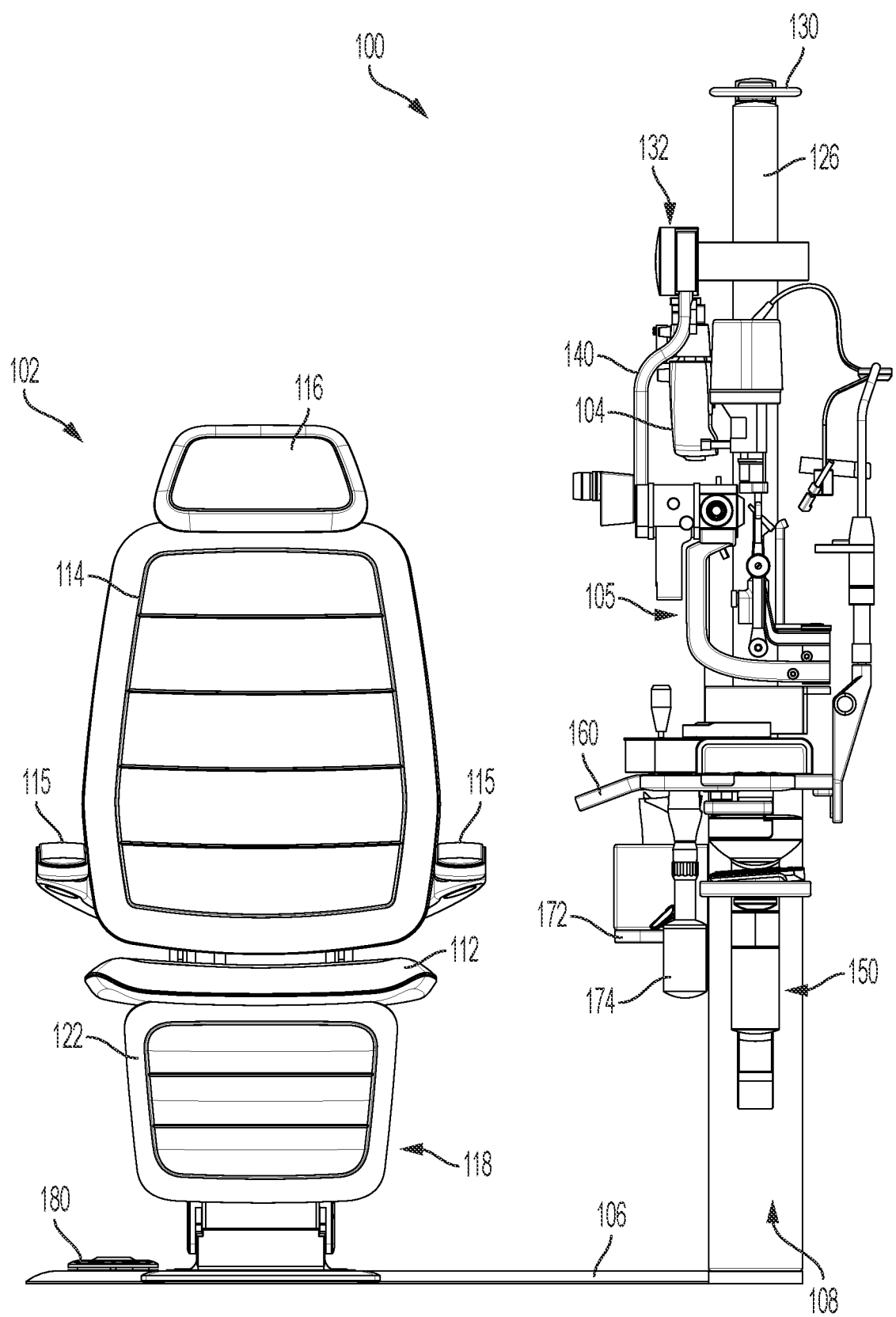
FIG. 3 is a front elevational view of integrated medical equipment including a patient support and procedure equipment supported by a procedure equipment support.
Figure 4:
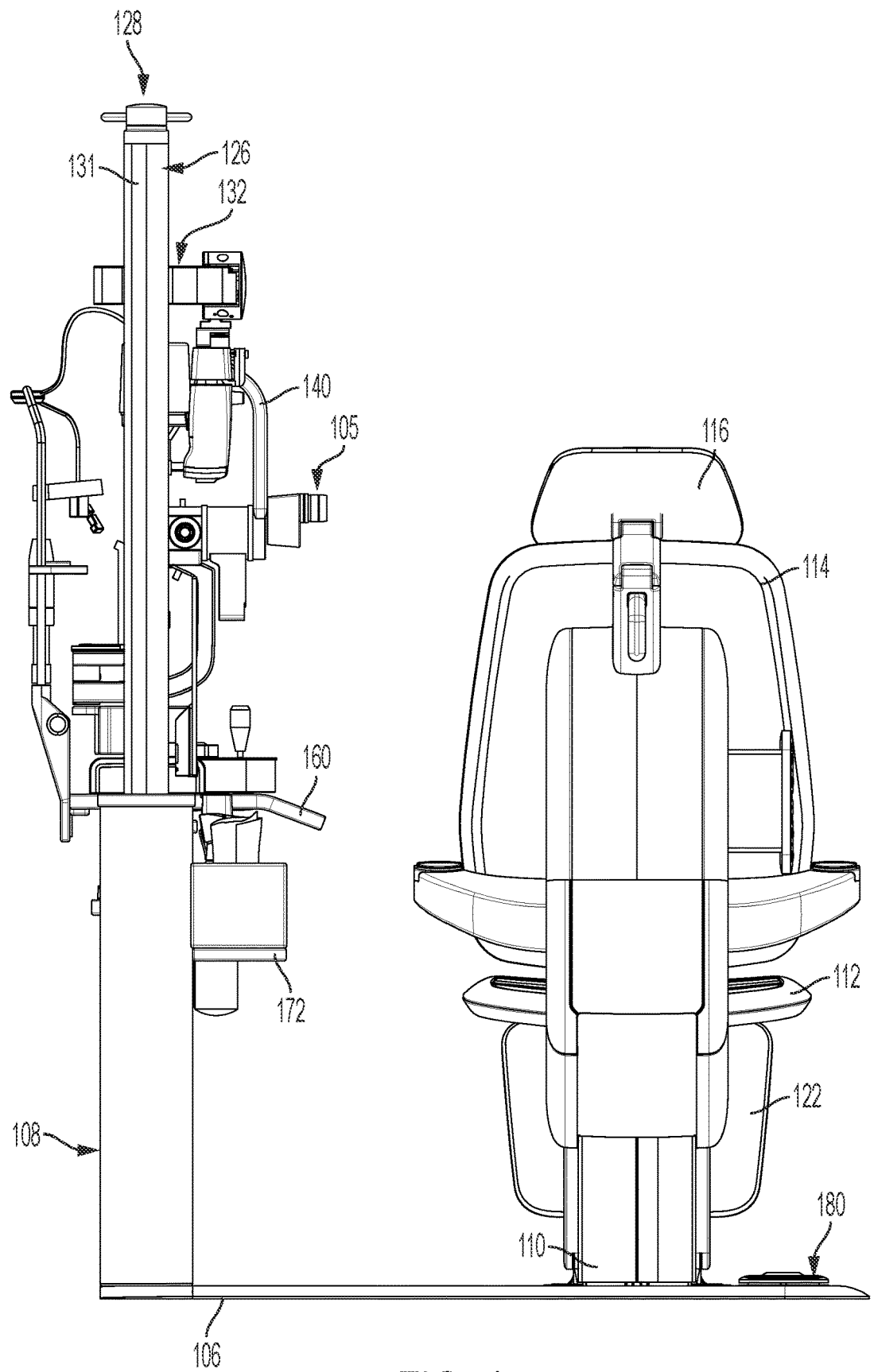
FIG. 4 is rear elevational view of integrated medical equipment including a patient support and procedure equipment supported by a procedure equipment support.

A platform support arm 150 (see also FIG. 2) is slidably coupled to the column 124 and configured to move in a direction 152, to raise and lower a first platform 154 and a second platform 156 (see FIG. 2). Each of the first platform 154 and the second platform 156 are further rotatably coupled to a neck 158 of the platform support arm 150. Each of the first platform 154 and the second platform 156 are separately rotatable about an axis of the neck 158. In one embodiment, the first platform 154 supports a tray 160 configured to support the slit lamp 105. Other trays to support other types of medical instruments are contemplated. The second platform 156 is configured to support a keyboard tray 162 for supporting a keyboard 164.

The column 124 includes a housing 165 having a relatively flat top surface 166 from which a monitor arm 1302 extends. The monitor arm 1302 is configured to rotatably support a monitor 170 configured to display images for use by the medical professional as well as the patient.

The housing 165 further supports a table 172 configured to support various items used by a patient before, during, or after completion of the procedure. In one embodiment, the table 172 is rotatably coupled to the housing 165 by hinges. A device holder 174, also supported by the housing 165, includes a plurality of instrument wells each of which is configured to hold an instrument used by the medical professional when performing a procedure. In one embodiment the device holder 174 is a charger for charging the instruments supported by the device holder.

Figure 5:
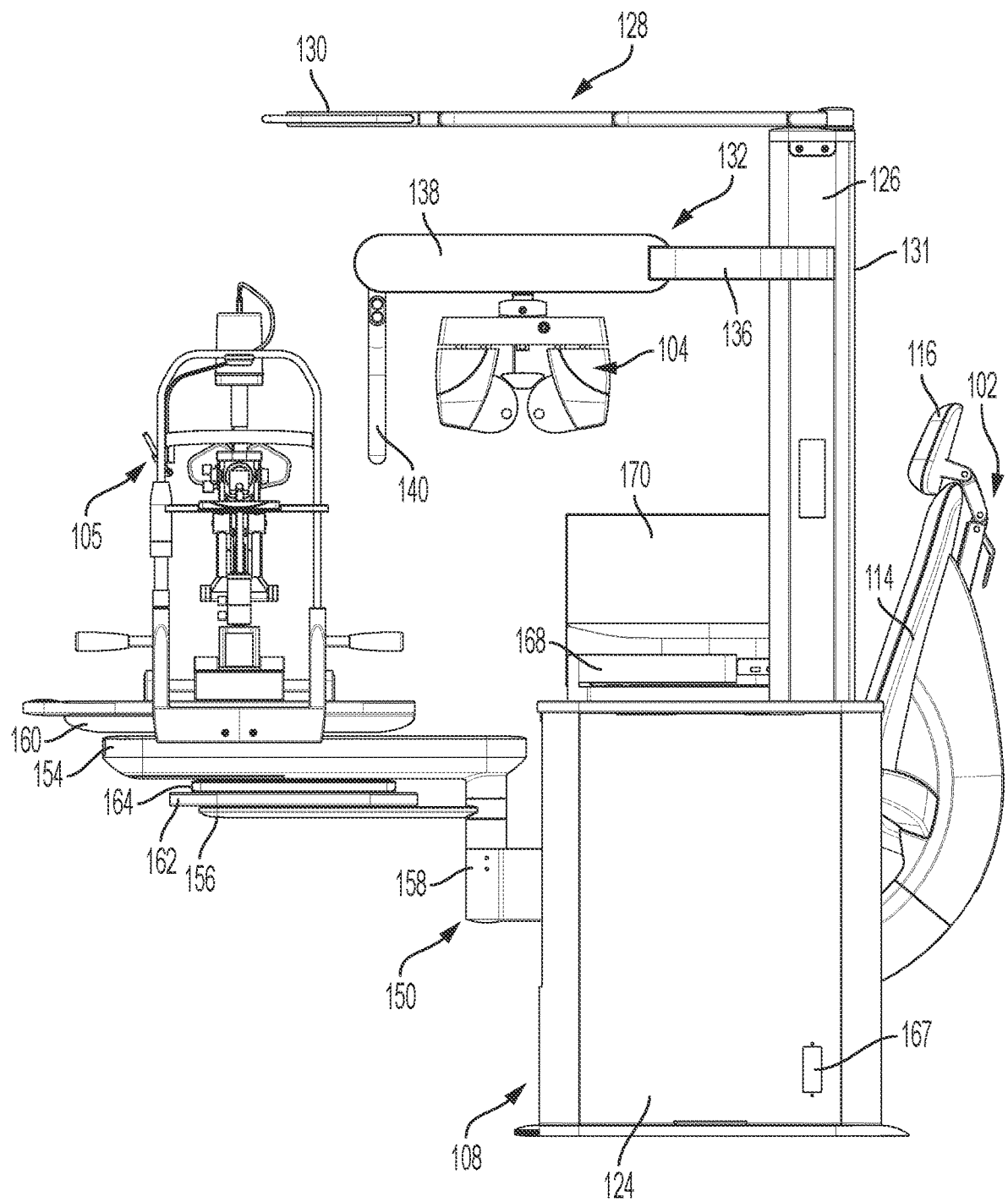
FIG. 5 is a second side elevational view of integrated medical equipment including a patient support and procedure equipment supported by a procedure equipment support.

The housing 165 includes a cavity defining an interior space configured to hold one or more motors, power supplies, and wiring cables. For instance, each of the arms 132 and 150 are driven by motors (not shown) configured to move the arm 132 along the direction 134 and the arm 150 along the direction 152. Each of the phoropter 104, the slit lamp 105, the light 130, the monitor 170, and the charging station 174, in one or more embodiments, are coupled to electrical cabling running through the respective support arms or the housing 165, to one or more power supplies or to 120 volt power supplied by the building in which the integrated medical equipment is located. In one embodiment, the housing 165 supports an electrical outlet 167 for connecting to the building 120 volt power. (See FIG. 5). In one embodiment, the light 130 is an LED light and consequently does not require 120 volt power but some power less than 120 volts. In this embodiment, a power supply coupled to the 120 volt power supplies the required light voltage. In other embodiments, one or more medical devices include an appropriate power supply and are directly coupled to 120 volt power that is supplied to the housing 165.

The housing 165 includes a generally rectangular configuration wherein the longer sides extend between curved edges defining the shorter sides. One of the longer sides 176, that supports the table 172 and the device holder 174, faces the leftmost arm 115 of the chair 102 (as illustrated) by a predetermined distance to enable the patent to use the table 172 for personal items. Since the column 124 is relatively narrow between the long sides, the integrated medical equipment 100 is configured to be placed against a wall of a room to provide a compact footprint with the base 106.

The integrated medical equipment further includes a chair controller 180 having one or more controls to adjust the position of the chair with respect to the base 106. In one embodiment, the chair controller 180 includes a height button to adjust the height of the chair, a tilt button to adjust the tilt of the chair, and a home button to return the chair to a home position. The home position is configured to locate the height of the chair so that the footrest 123 rests on and is flush with the floor 120. By locating the footrest 123 on the floor in the home position, a patient is fully supported by a stable platform, the floor 120, since the floor provides solid support for the footrest 123. The patient, therefore, does not experience an instability that results from the footrest 123 being spaced from the floor in the home position when entering or exiting the chair.

In one embodiment, the chair controller 180 is a wireless foot operated controller and is located at a docking station included in the base 106. In one or more embodiments, the wireless foot operated controller 180 communicates by wireless technology, such as Bluetooth, with a transceiver located at the column 165. The docking station is wired through the housing 165 and provides power to the docking station for powering the chair controller. In other embodiments, the docking station includes a charger for charging a battery located in the controller 180, so that the controller 180 is movable to other locations to accommodate the medical professional's preferred working arrangement.

One or more handheld remote controllers 182 are located at a controller station located on the chair 102. Each of the one or more controllers 182 is configured to enable an individual to adjust each of the controllable functions as described herein. In one or more embodiments, the controller station is a charging station for the controllers 182.

Figure 6:
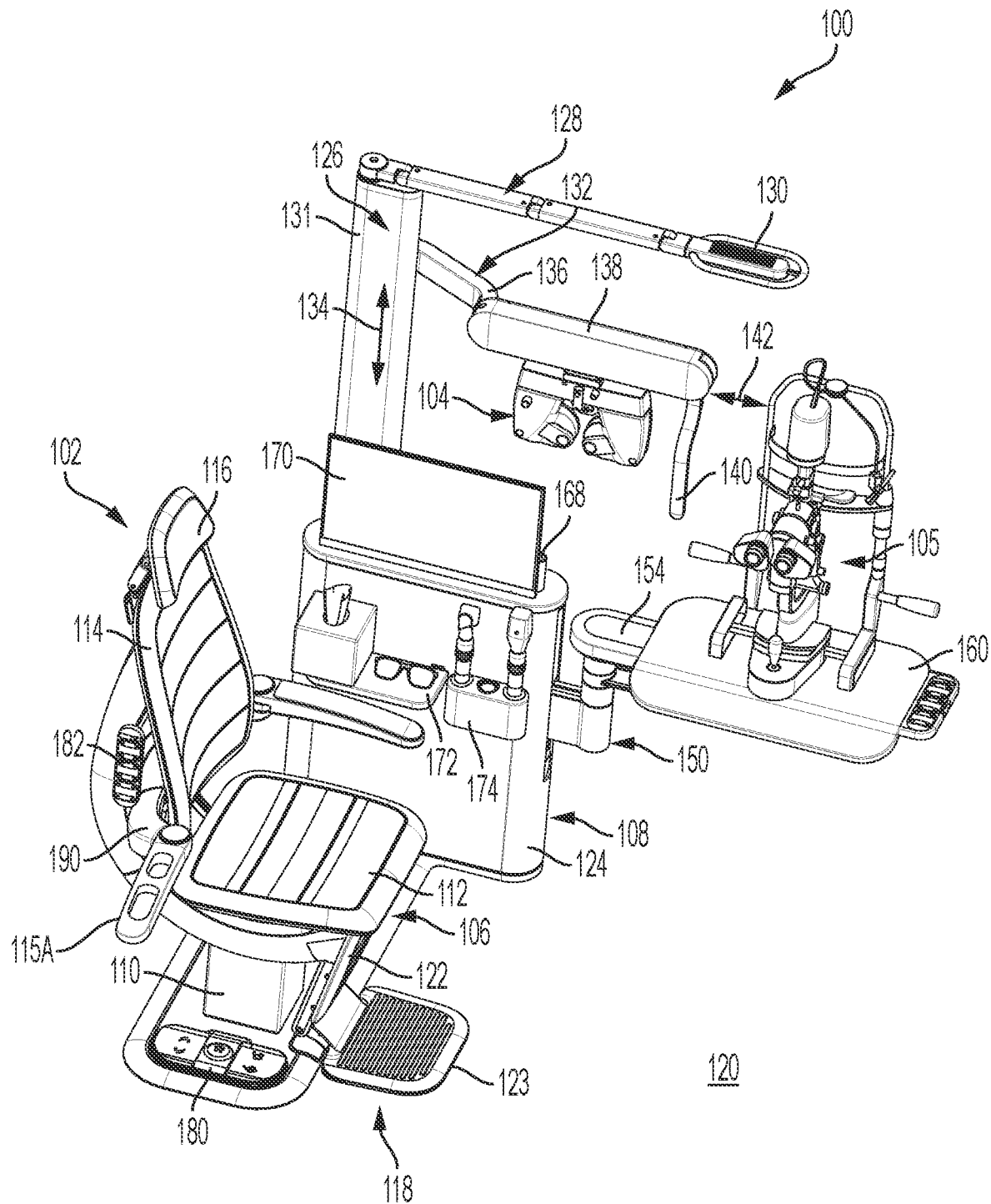
FIG. 6 is a top perspective view of integrated medical equipment including a patient support having a patient arm support in an open position.
Figure 7:
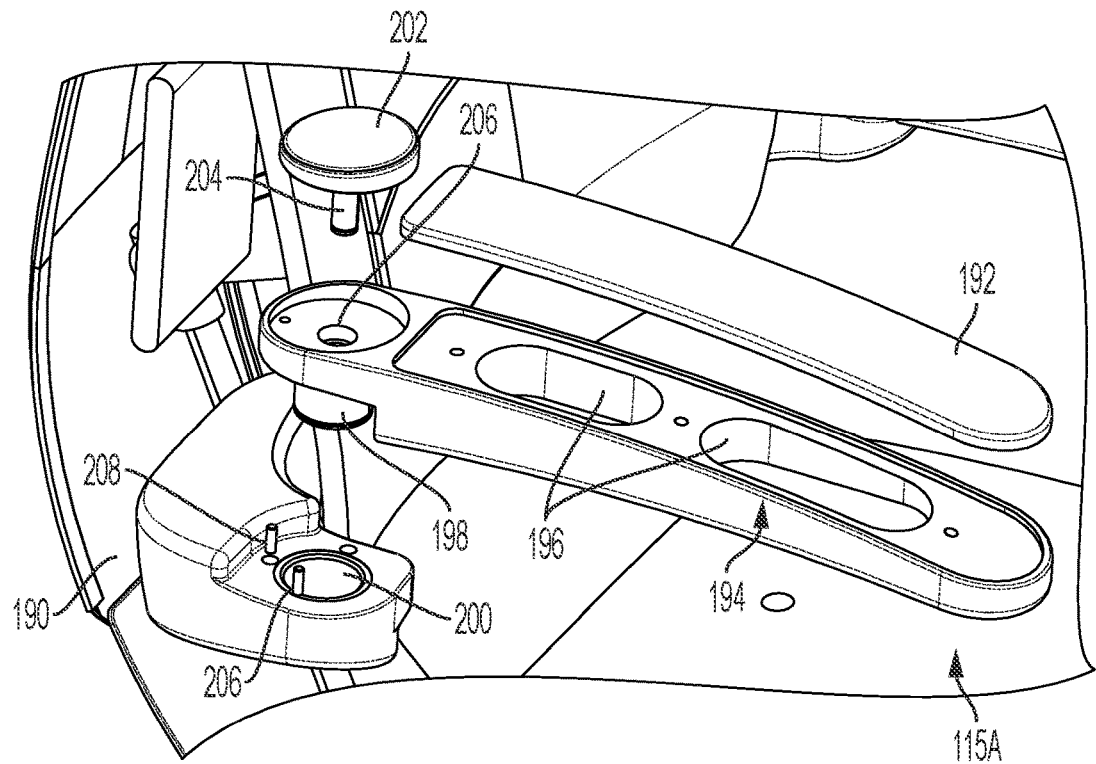
FIG. 7 is an exploded top perspective view of a patient arm support in a closed position.
Figure 8:
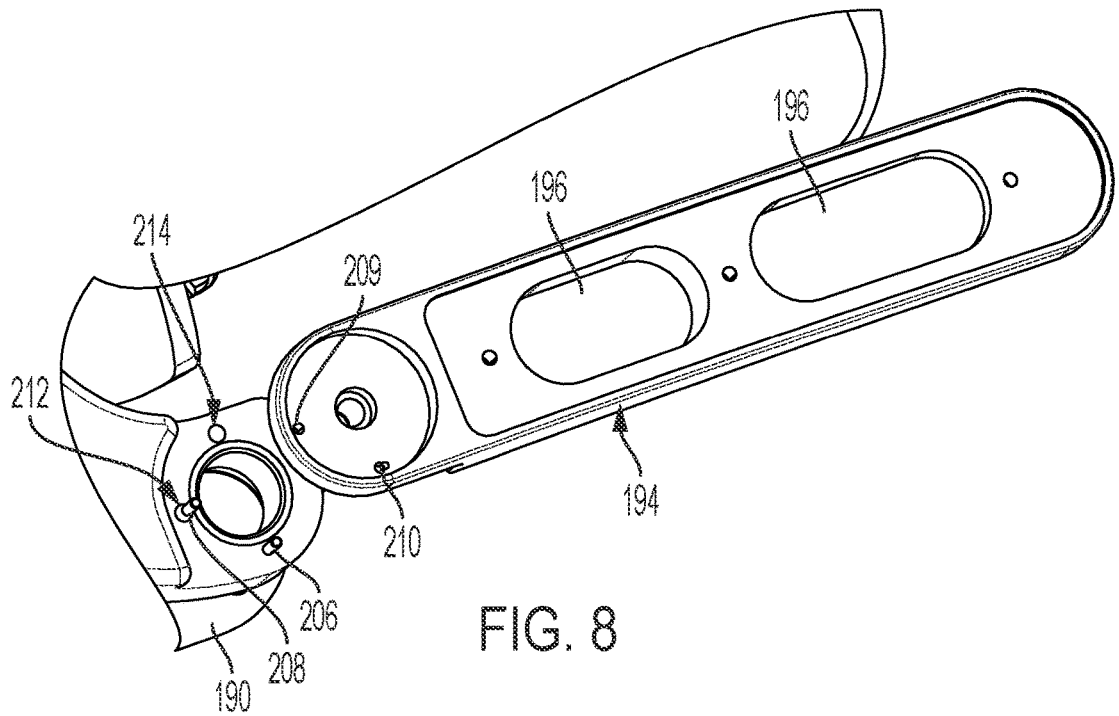
FIG. 8 is a top perspective view of a portion of the patent arm support of FIG. 7.

FIG. 6 is a top perspective view of the integrated medical equipment 100 including the patient support 102 having the left arm 115A (as illustrated) in an open position. In the open position, the arm is located to extend generally along a plane of the back 114. In contrast and as illustrated in FIG. 1, the arm 115A is located in a closed position. In the open position, the arm 115A of FIG. 6 is positioned to enable an individual to enter and to exit the chair 102 without having to maneuver about the arm in a closed position. The arm 115A is rotatably coupled to back support 190, which also supports the back 114.

The arm 115A includes a top arm support 192, configured to support an individual's arm, and a bottom arm support 194 upon which the top arm support 192 is located. The top arm support 192 is not illustrated in FIG. 6. The bottom arm support 194 includes cutouts 196, which in one embodiment, reduce the weight and the material of the arm 115, while still being sufficiently rigid to support a patient's weight when entering and exiting the chair 102. The bottom arm support 194 includes a boss 198 which extends generally perpendicular to a long length of the arm 115 and which includes a diameter configured to fit within an aperture 200 formed in the back support 190. When the boss 198 is seated in the aperture 200, the arm 115 rotates about an axis extending generally perpendicular to the long length of the arm 115A.

A cap 202 includes a shaft 204 configured to extend through an aperture 206 of the bottom arm support 196. In one embodiment, the shaft 204 is configured to receive a connector, such as a screw, which extends through the aperture 200 and into the shaft 204.

Rotation of the arm about the rotational axis is limited by a first pin 206 and a second pin 208. The first and second pins 206 and 208 extend at least partially through holes 209 and 210 located in the bottom arm support 194. The back support 190 includes holes 212 and 214 which are configured to at least partially receive pins 206 and 208. Interaction between the pins 206 and 208 with the holes 212 and 214 provide for a first detent to hold the arm in the closed position and a second detent to hold the arm in the open position.

In one aspect of this disclosure, when the arm is in the closed position, pin 206 and hole 210 of the arm support 194 may not be aligned with either of the holes 212, 214 while the pin 208 and hole 209 may be aligned with the hole 212 of the back support 190. In this configuration, pin 208 may be at least partially positioned within the hole 212 to maintain the armrest 115A in the closed position.

Alternatively, when the arm is in the opened position, pin 206 and hole 210 of the arm support 194 may be aligned with the hole 212 while the pin 208 and hole 209 may be aligned with the hole 214 of the back support 190. In this configuration, pins 206, 208 may be at least partially positioned within the respective holes 212, 214 to maintain the armrest 115A in the closed position.

Figure 9:
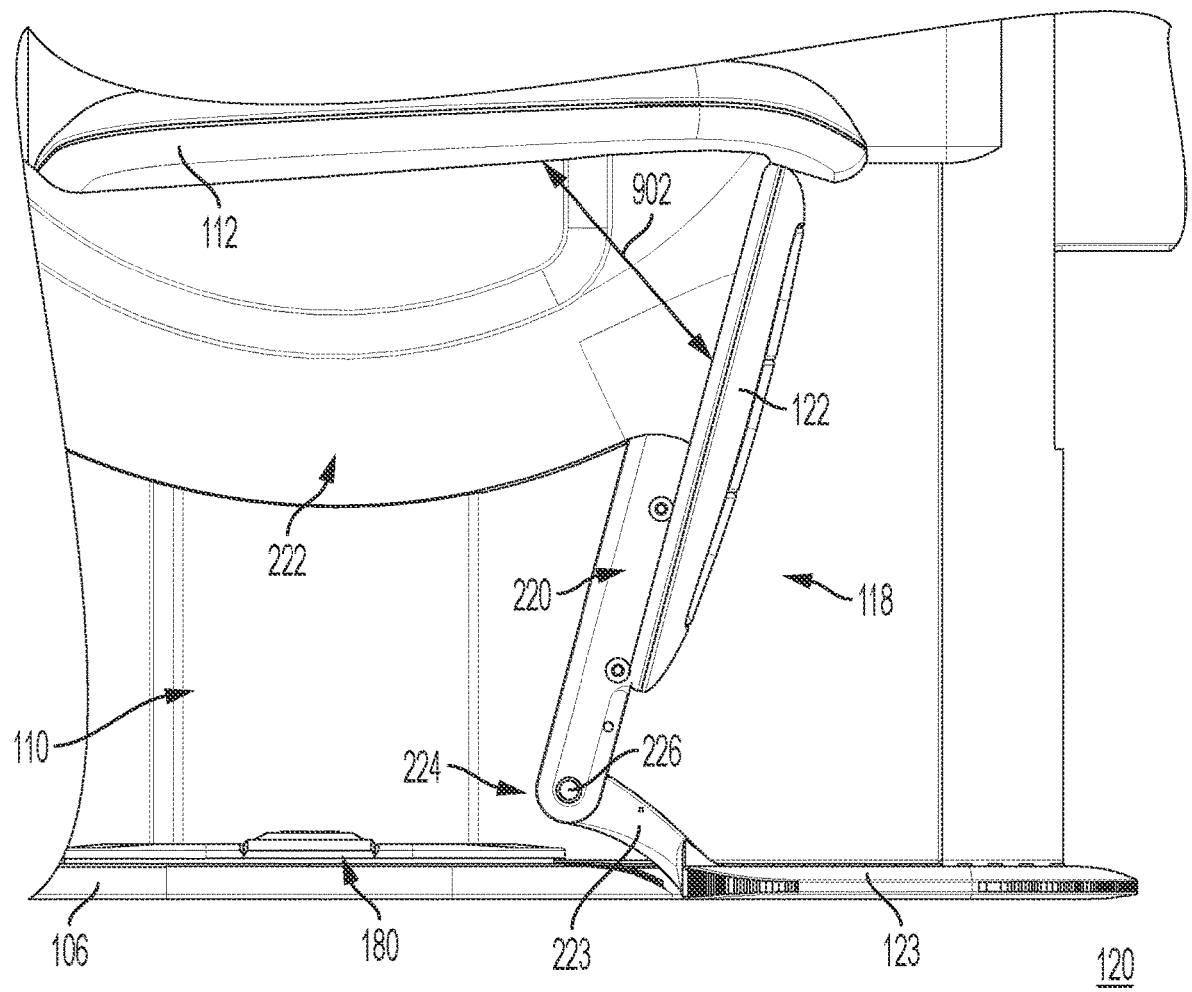
FIG. 9 is a side elevational view of a portion of a patient support showing a legrest.

FIG. 9 is a side elevational view of a portion of a patient support showing the leg rest 118. The leg rest 118 includes a calf support 122 extending from the seat 112 and a footrest 123 extending from the calf support 122. The calf support 122 is fixedly coupled to a leg rest bracket 220 which is fixedly coupled to a seat support 222 which also supports the seat 112. A footrest bracket 223, which is fixedly coupled to the footrest 123, is rotatably coupled to a terminating end 224 of the leg rest bracket 220. The footrest 123 is rotatable about a pivot 226 such that footrest 123 is located at the floor 120 when the pedestal 110 has been set to height to accommodate a seated individual. An interface between the bracket 220 and the bracket 223 includes a stop that prevents substantial rotation of the footrest 123 with the calf support 122. Consequently, when the chair 102 is raised, the footrest 123 remains at a relatively flat position with respect to a plane of the floor 120 to provide support for an individual's feet.

The calf support 122 is angled an offset angle 902 relative to the seat 112. The offset angle 122 may be such that the user's feet are at least partially positioned under the seat 112 when the user's calves are contacting the calf support 122. The offset angle 902 of the calf support 122 allows the user to more easily stand from the seated position and vice versa by allowing the user to position their feet at least partially under the seat 112. This allows the user to more easily align their body with their center of gravity while transitioning form the standing to seated position or while transitioning form the seated to standing position. Accordingly, by positioning the calf support 122 at the offset angle 902 it may be easier for the user to transition between the seated and standing positions of the patient chair 102.

Figure 10:
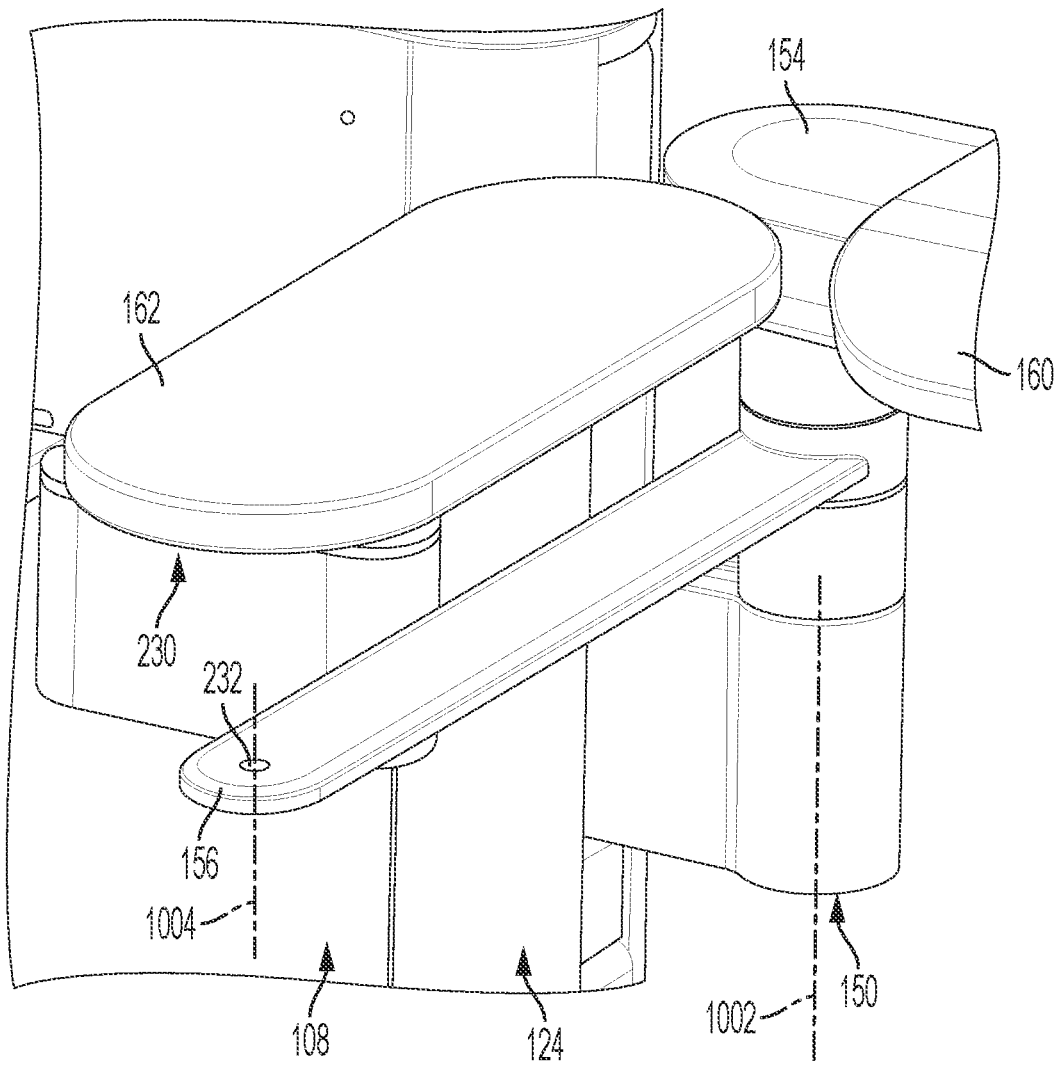
FIG. 10 illustrates the platform support arm including the first platform and a second platform disposed at an angle with respect to the first platform.

FIG. 10 illustrates the platform support arm 150 including the first platform 154 and the second platform 156 disposed at an angle of approximately 90 degrees with respect to the first platform 154. As seen in FIG. 2, the second platform 156 moves from the illustrated position of being aligned with the first platform 154, to the illustrated position of FIG. 10 rotated approximately 90 degrees therefrom along a support arm axis 1002. The keyboard tray 162 is shown in an exploded view with the second platform 156 to illustrate an aperture 232 configured to engage a swivel connector 230 in the keyboard tray 162. The aperture 232 and swivel connectors 230 may correspond with one another to allow the keyboard tray 162 to rotate along an aperture axis 1004 relative to the second platform 156. With the swivel connector and the 90 degree movement of the second platform 156, the keyboard 164 is positionable in a plurality of locations to accommodate location preferences of the health care professional.

In one aspect of this disclosure, detents or the like may be defined between the second platform 156 and the platform support arm 150 to establish preset positions of the second platform 156. More specifically, a first preset position may be defined when the second platform 156 is in a first orientation as illustrated in FIG. 1 and a second preset position may be defined when the second platform 156 is in a second position as illustrated in FIG. 10. The detents may provide a rotational range of the second platform 156 in which an increased torque is required to further rotate the second platform 156. In other words, the second platform 156 may easily pivot relative to the platform support arm 150 about the support arm axis 1002 until it is positioned in one of the preset positions, wherein an increased torque is required to move the second platform 156 out of the preset positions.

Figure 11:
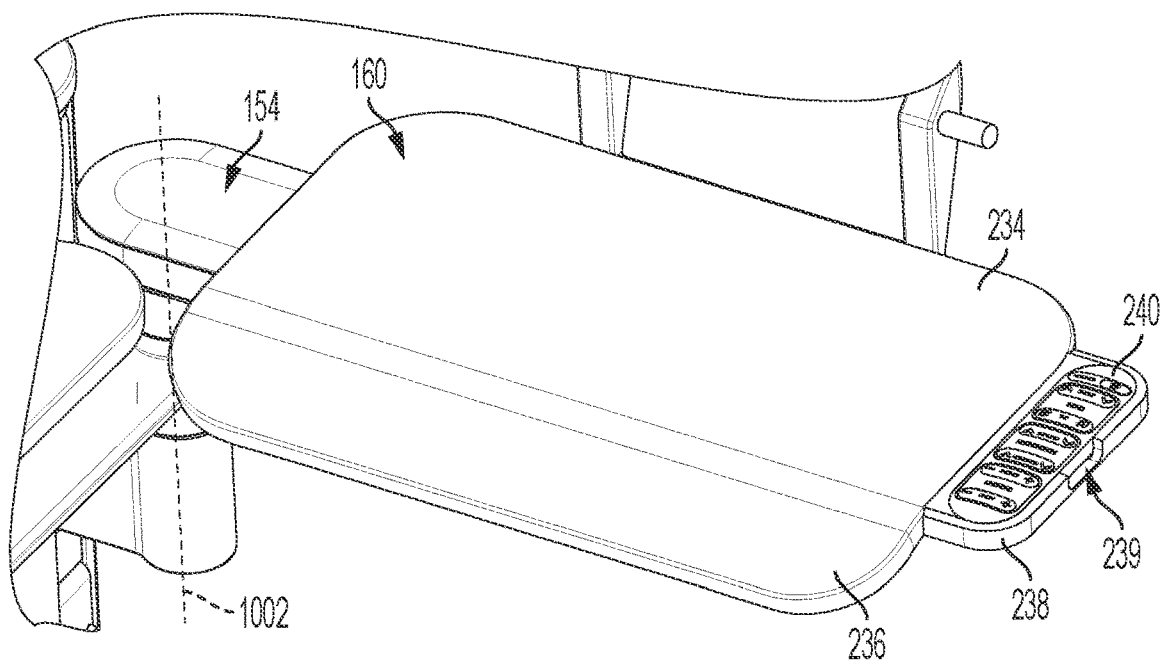
FIG. 11 illustrates the first platform supporting a tray.

FIG. 11 illustrates the first platform 154 supporting the tray 160. The tray 160 includes a planar portion 234 defining a substantially flat surface configured to support a medical instrument, such as the slit lamp 105. An angled portion 236 is coupled to and extends from the portion 234 in a downward angle toward the floor 120. In one embodiment, the angled portion 236 is inclined with respect to the planar portion 234 at about 10 degrees. Other angles of inclination are contemplated. The angled portion 236 is configured to support some weight of the medical professional, particularly the arms of the professional, while operating the medical equipment. In other embodiments, the angled portion 236 is movable with respect to the planar portion 234 to accommodate other angles of inclination preferred by the practitioner. The tray 160 includes an extension 238 coupled to the planar portion 234 defining a cavity 239 configured to receive a handheld remote controller 240. In one embodiment, the controller 240 is configured to control the lighting 130 and the medical device arm 132, the positions of the chair 102, the various instruments including the phoropter 104 and slit lamp 105, and the monitor 170.

The first platform 154 may also be pivotal about the support arm axis 1002 to a plurality of angular positions there-around. The first platform 154 may rotate about the support arm axis 1002 to allow the physician or other user to position the tray 160 and any instruments thereon in front of a patient positioned in the patient chair 102. Further, detents or the like may be defined between the first platform 154 and the platform support arm 150 to establish preset positions of the first platform 154. More specifically, a first preset position may be defined when the first platform 154 is in a first orientation as illustrated in FIG. 1 and a second preset position may be defined when the first platform 154 is in a second position that is rotationally offset from the first position. The detents may provide a rotational range of the first platform 154 in which an increased torque is required to further rotate the first platform 154. In other words, the first platform 154 may easily pivot relative to the platform support arm 150 about the support arm axis 1002 until it is positioned in one of the preset positions, wherein an increased torque is required to move the first platform 154 out of the preset positions.

Figure 12:
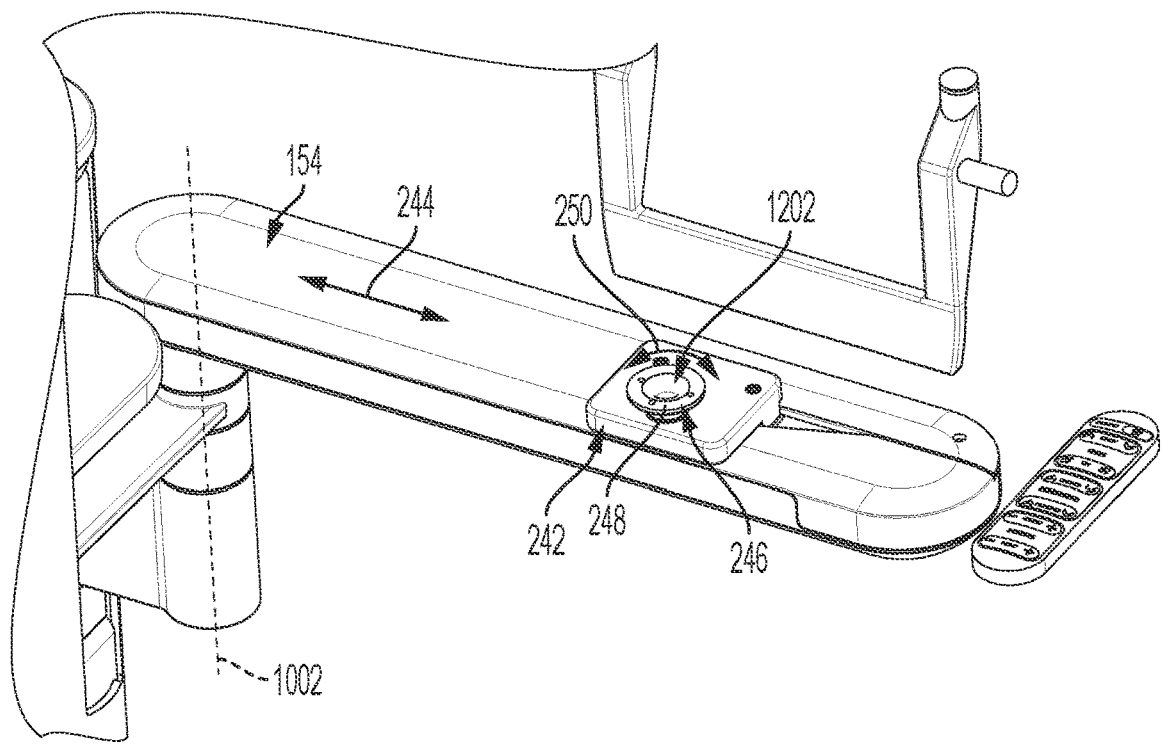
FIG. 12 illustrates a first platform having a movable support.

As illustrated in FIG. 12, the first platform 154 includes a movable support 242 configured to move along a direction 244 to enable positioning of the tray 160 and consequently positioning of the instrument to a preferred location for the professional. The movable support 242 includes a rotatable support having a flange 248, which is fixedly coupled to the tray 160. The location of the supported instrument is therefore locatable along the direction 244 as well as being rotatable about an angle of rotation 250 defined by the support 264.

The flange 248 may also have a hollow passage 1202 positioned there through at the pivot axis of the flange 248. The hollow passage 1202 may provide a wire routing location for wires from the instrument positioned on the tray 160. Further, the tray 160 may have wire passages defined therein along a lower surface of the tray 160. The wire passages of the tray 160 and the hollow passage 1202 of the flange 248 allows instruments requiring a wired connection to be placed on the tray 160 while strategically routing the wires through the wire passages of the tray 160, through the hollow passage 1202 of the flange 248, into an inner cavity of the first platform 154, into a cavity of the platform support arm 150, into the column 124, and then routed to a power source or other component of the integrated medical equipment 100.

In one aspect of this disclosure, at least some of the wires for an instrument positioned on the tray 160 may be routed as described above to limit binding, wear, and length of the required wires. More specifically, by routing the wire through the hollow passage 1202 which is defined along the pivot axis of the flange 248, the tray 160 can pivot about the flange 248 as described above without substantially binding, knotting, severing, or otherwise compromising the wiring. In one aspect of this disclosure, the tray 160 may be limited from rotating more than three-hundred and sixty degrees to ensure that any wires routed through the flange 248 are not compromised by over rotation.

Similarly, any wires from the first or second platform 154, 156 may be routed through the platform support arm 150 in order to substantially hide the wires from being visible to the user while also protecting the wires as described above. Further, a passage may be defined between the platform support arm 150 and the housing 165 to allow wires to be routed from either platform 154, 156 to an internal cavity of the housing 165 via the platform support arm 150.

Figure 13:
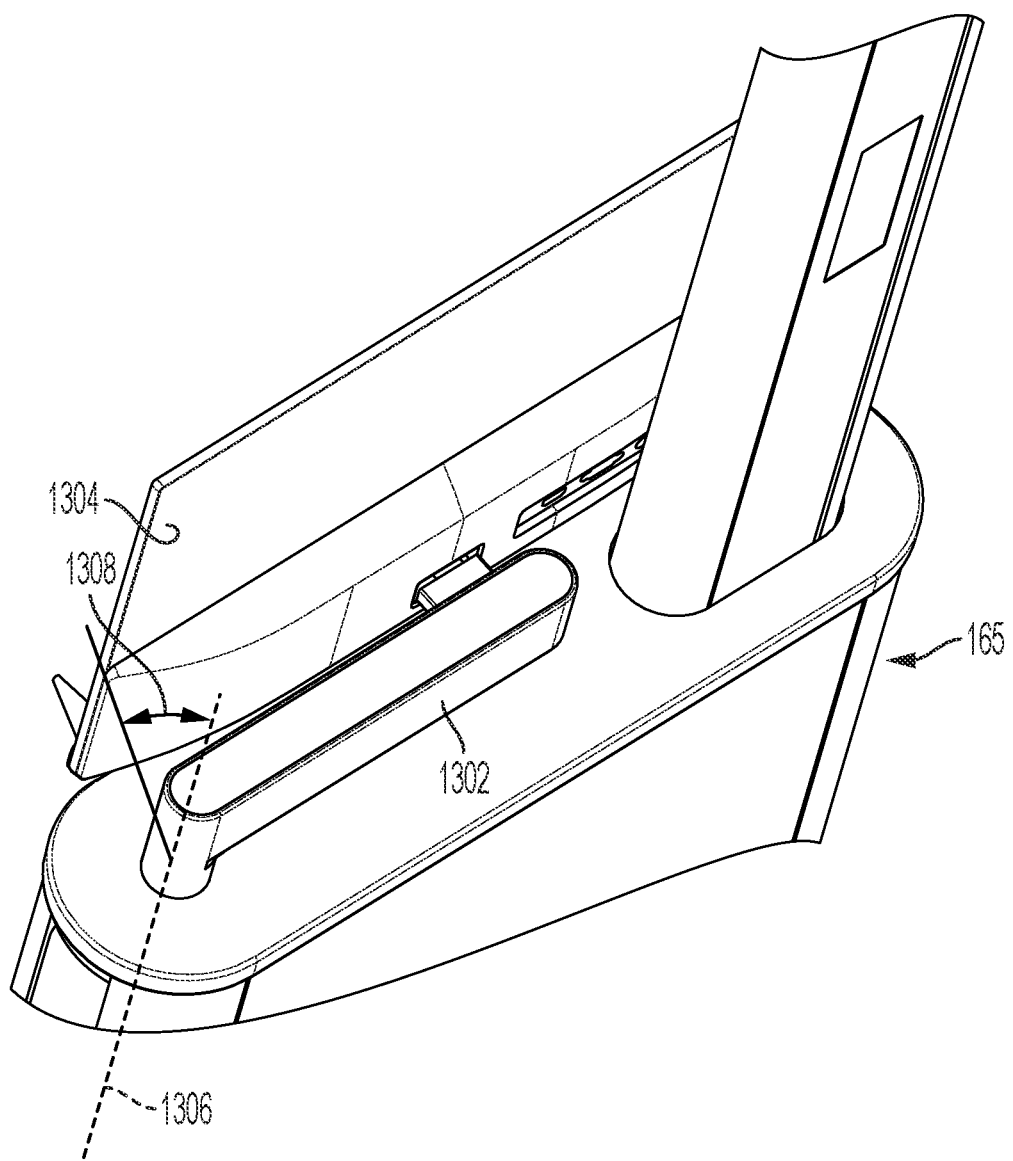
FIG. 13 illustrates a monitor arm.
Figure 14:
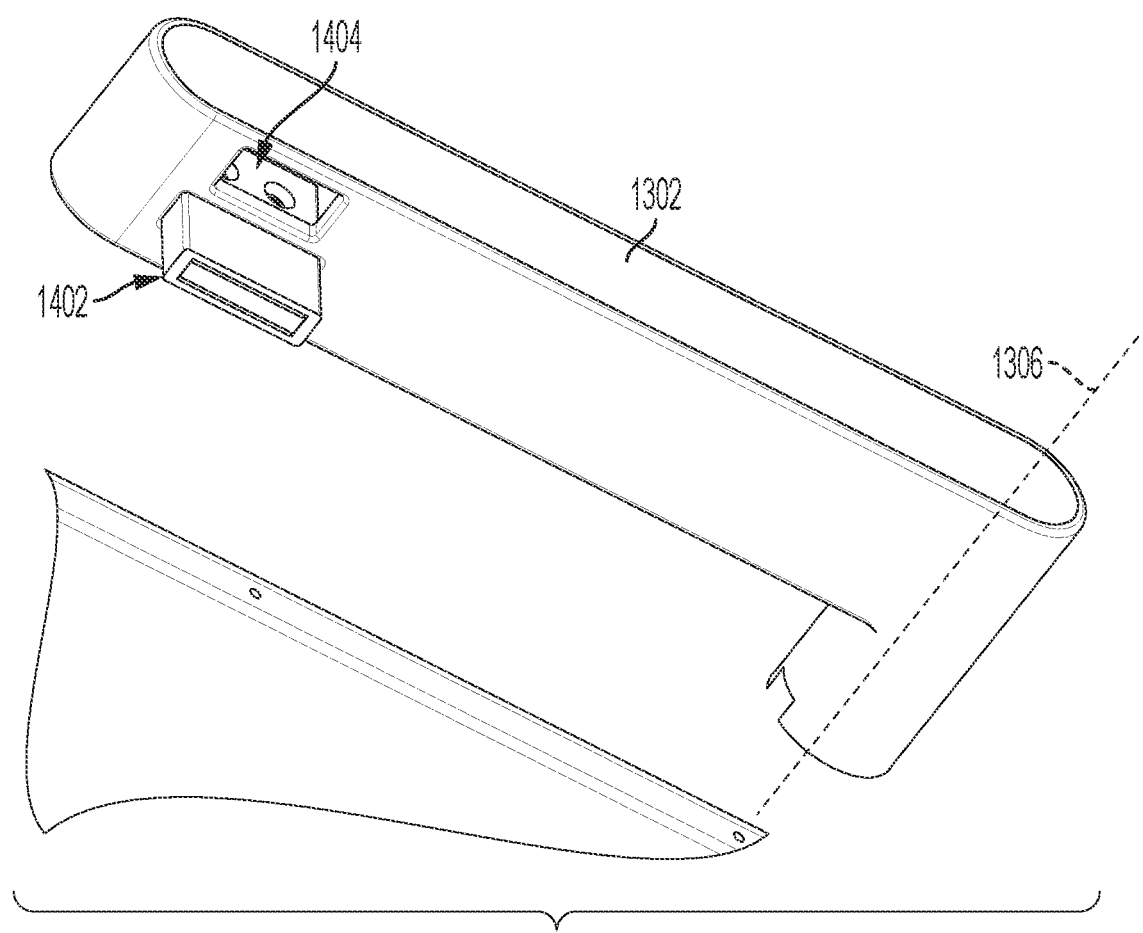
FIG. 14 illustrates an isolated view of the monitor arm of FIG. 13.

Referring now to FIGS. 13 and 14, a monitor arm 1302 is illustrated coupled to the housing 165 on one end and to a monitor 1304 on the other (monitor removed in FIG. 14). The monitor arm 1302 is pivotally coupled to the housing 165 about a monitor axis 1306. The monitor arm 1302 may pivot a monitor angle 1308 about the monitor axis 1306 from a patient viewing position as shown in FIG. 13 to a professional viewing position. In the patient viewing position, the monitor 1304 may be substantially aligned with the housing 165 to allow the patient to view the monitor 1304 from the chair 102. When the monitor 1304 is rotated the monitor angle 1308 however, the monitor 1304 may be angled relative to the housing 165 towards the professional that may be seated across from the patient. When the monitor 1304 is rotated the monitor angle 1308, the professional may more easily view the monitor. Further, in one aspect of this disclosure the monitor angle 1308 may be such that both the patient and the professional can simultaneously view the monitor 1304 to allow the professional to explain the contents of the monitor 1304 to the patient.

The monitor arm 1302 may also have a monitor coupler 1402 defined thereon and configured to couple the monitor 1304 to the monitor arm 1302. The monitor coupler 1402 may utilize any known method for coupling a monitor to a stand, wall, or other device. Further, the monitor arm 1302 may define a hollow cavity therein that has an access port 1404 that provides access to the hollow cavity. The access port 1404 may be positioned proximate to the monitor coupler 1402 and sized to allow wires from the monitor 1304 to become positioned through the monitor arm 1302 and into the housing 165. The monitor arm 1302 may define a cable routing cavity that routes any cables positioned thereon through the cable monitor arm 1302 along the monitor axis 1306 similarly to the wire routing for the platforms 154, 156. More specifically, by routing the wires along the monitor axis 1306 the wires may allow the monitor arm 1302 to pivot about the monitor axis 1306 without damaging the wires.

Figure 15:
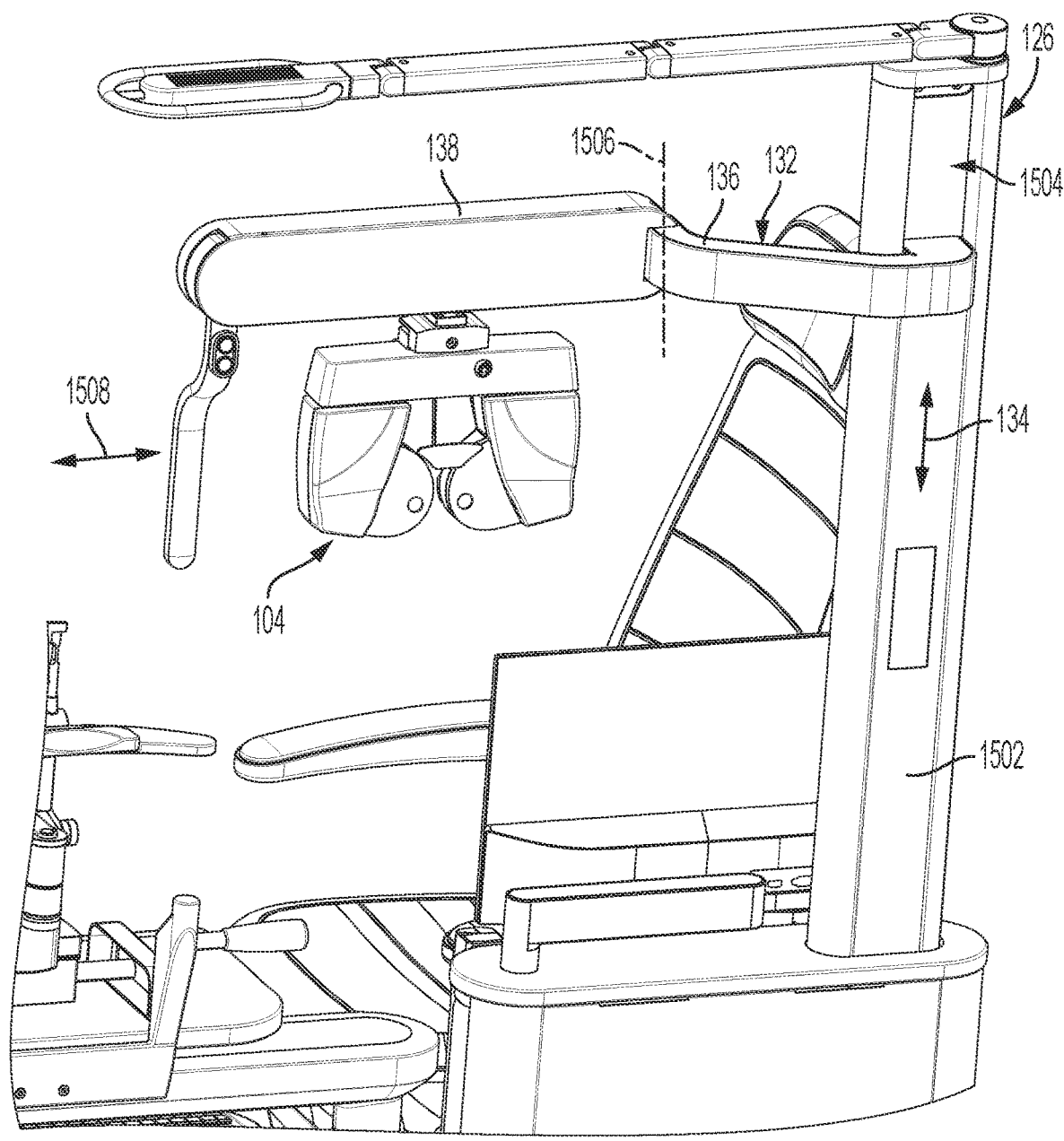
FIG. 15 illustrates a perspective side view of the integrated medical equipment of FIG. 1.

Referring now to FIG. 15, the medical device arm 132 is more clearly illustrated. The medical device arm 132 may move in substantially the vertical direction 134 along the tower 126. The medical device arm 132 may be coupled to a slide 1502 that moves along a rail 1504 of the tower 126 in the vertical direction 134. The movement of the medical device arm 132 in the vertical direction 134 allows the professional to position the phoropter 104 at a vertical distance that corresponds with the patient's eyes.

In addition to being movable in the vertical direction 134, the second arm 138 of the medical device 132 may pivot about an arm axis 1506 defined by the first arm 136. The arm axis 1506 may be defined to pivot the second arm 138 into a location aligned with the patient to thereby allow the phoropter or other device to be positioned proximate to the patients face.

In addition to being adjustable in the vertical direction 134 via the slide 1502 and rail 1504 configuration, and pivotal about the arm axis 1506, the phoropter 104 may also be slidably coupled to the second arm 138 to allow the phoropter 104 to move in the second direction 1508. The phoropter 104 may move in the second direction 1508 to allow the professional to further adjust the phoropter 104 to ensure it is positioned at a location that is ideal for both the professional and the patient.

Figure 16:
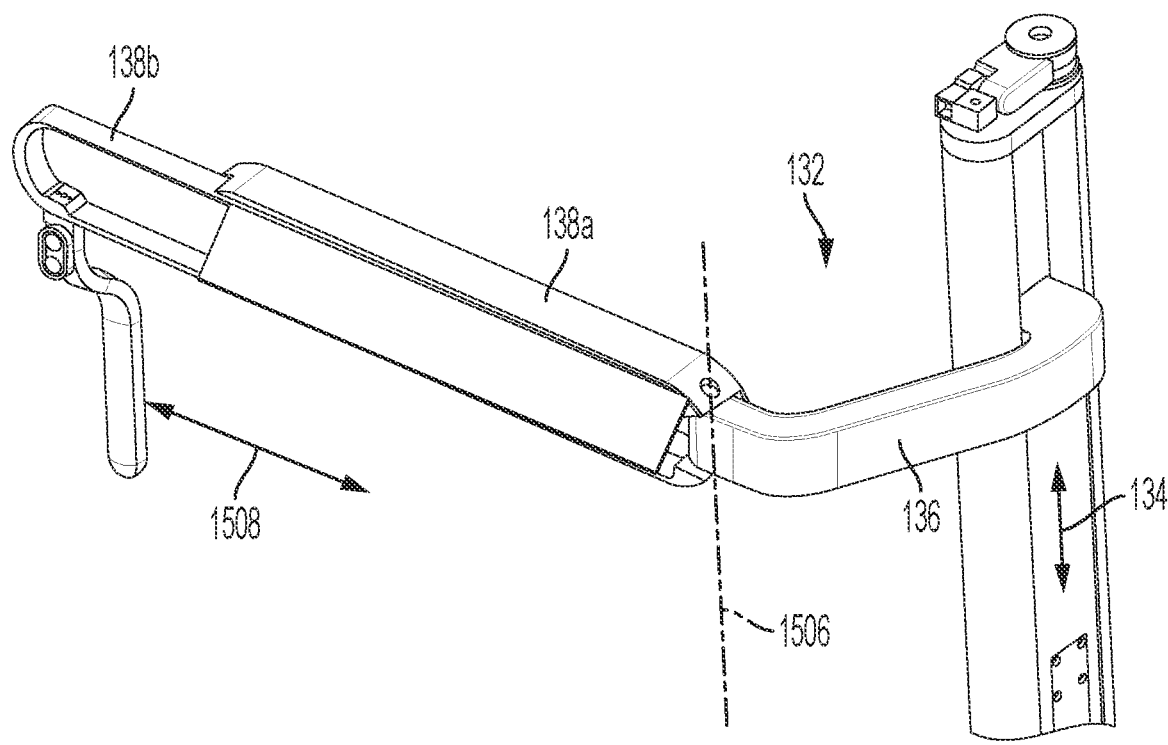
FIG. 16 illustrates an extended view of a second arm.

Referring now to FIG. 16, an outer second arm 138a and an inner second arm 138b is illustrated. The inner second arm 138b may slide in the second direction 1508 relative to the outer second arm 138a. More specifically, the inner second arm 138b may be slidably coupled to the outer second arm 138a via rails, linear bearings, or any other device that allows linear movement. Further, the phoropter 104 (not illustrated in FIG. 16) may be coupled to the inner second arm 138b to move in the second direction 1508 therewith. Accordingly, the professional may adjust the phoropter 104 in the vertical direction 134, pivot the phoropter 104 about the arm axis 1506, and slide the phoropter 104 in the second direction 1508 to properly position the phoropter 104 or other device.

The first and second arm 136, 138, and slide 1502 may also be configured to define an internal wire routing passage to the housing 165 similar to the monitor arm 168 and the platforms 154, 156. More specifically, if a device is coupled to the inner second arm 138b that requires wired connectivity to any other portion of the medical equipment 100 or to an external device, the wire or wires can be routed through an internal cavity of the inner and outer second arm 138a, 138b, an inner cavity of the first arm 136, along a cavity of the tower 126, and into the housing 165. The wire routing may be such that enables the phoropter 104 or other device to move along any of the directions discussed herein without compromising the wires positioned therein.

Figure 17:
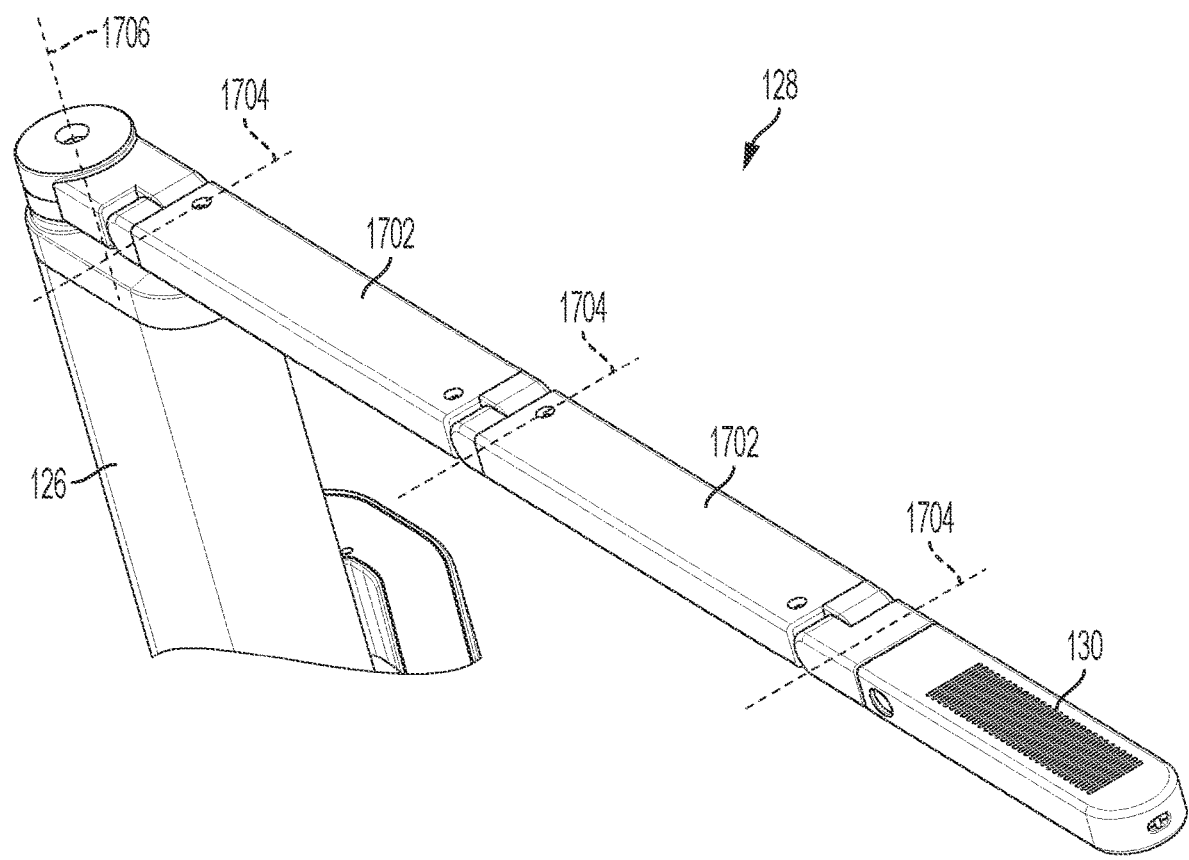
FIG. 17 is an elevated perspective view of a lamp assembly.

Referring now to FIG. 17, the illumination arm 128 is illustrated in more detail. The illumination arm 128 may have one or more segments 1702 pivotally coupled to the remaining portions of the illumination arm 128 about illumination axes 1704. Segments 1702 may pivot about the illumination axis 1704 to allow the examination light 130 to be repositioned along a substantially vertical plane. Further, the segments 1702 and examination light 130 may be pivotally coupled along a substantially vertical light axis 1706. The light axis 1706 may be defined partially through the tower 126 and allow the professional to rotate the examination light 130 about the vertical light axis 1706. Accordingly, the professional may reposition the light 130 both by rotating the illumination arm 128 about the light axis 1706 and by repositioning any one or more of the segments 1702 along the corresponding illumination axes 1704.

The examination light 130 may have wiring that is routed through internal cavities of the illumination arm 128 to the tower 126 and through the tower 126 into the housing 165. Similar to the platforms 154, 156, and the monitor arm 168, any wires needed for the examination light 130 may be substantially hidden in the internal cavities of the illumination arm 128, tower 126, and housing 165.

Figure 18:
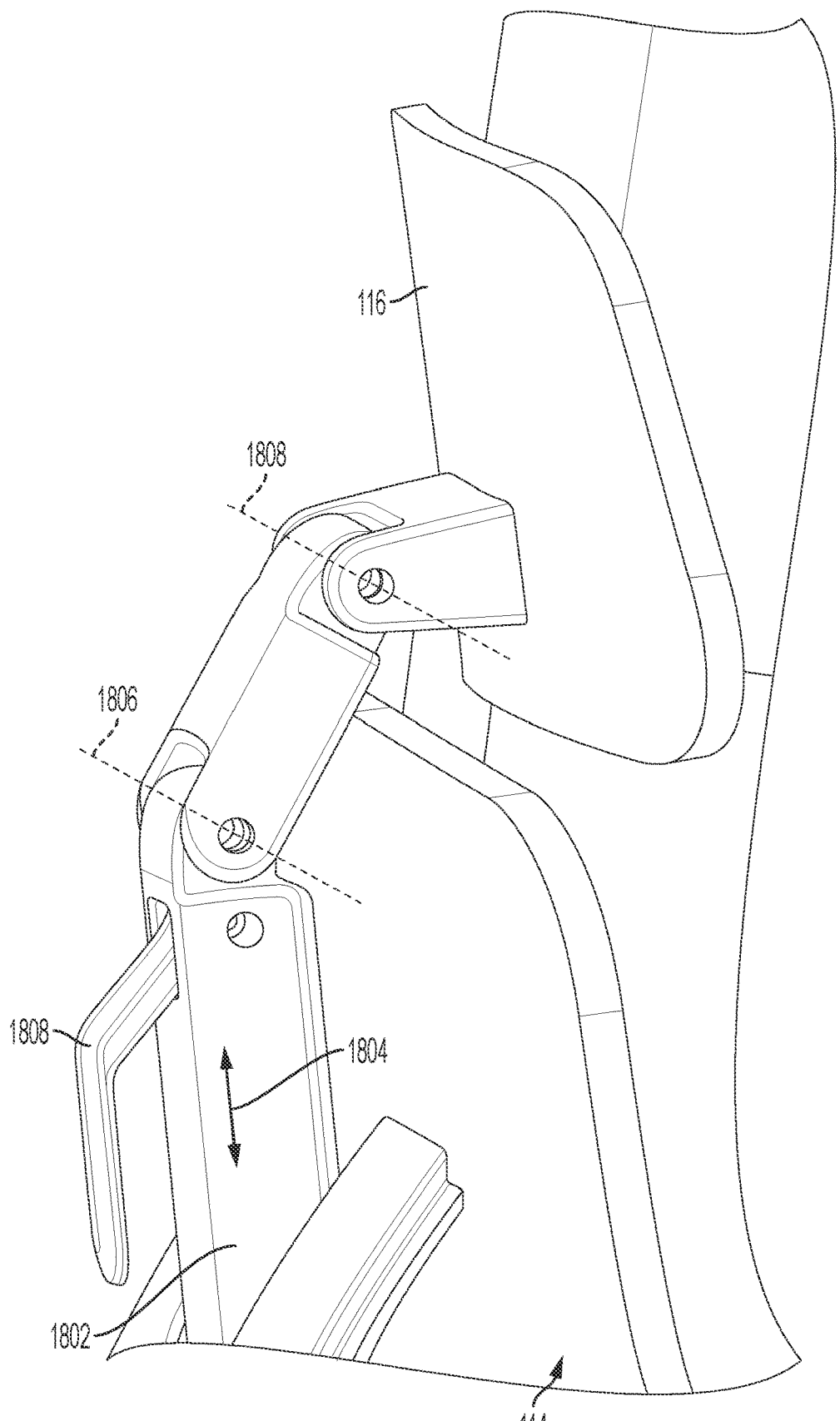
FIG. 18 is an elevated perspective view of a headrest assembly.

Referring now to FIG. 18, the headrest 116 is illustrated in more detail. In one aspect of this disclosure, the headrest 116 may be both pivotally and slidably repositionable relative to the back 114. More specifically, a sliding member 1802 may be slidable along a backrest direction 1804 to slidably reposition the headrest 116 coupled thereto. Further, the headrest 116 may be pivotally coupled to the sliding member 1802 along a first headrest axis 1806 and a second headrest axis 1808.

A release mechanism 1808 may be coupled to the sliding member 1802 to selectively allow the headrest 116 to slide along the backrest direction 1804 and rotate about the first headrest axis 1806. The release mechanism 1808 may pivot between a released position and a locked position. When the release mechanism is in the locked position, the headrest 116 may be substantially restricted from moving both along the backrest direction 1804 and about the first headrest axis 1806. Alternatively, when the release mechanism is in the released position, the headrest 116 may move both along the backrest direction 1804 and about the first headrest axis 1806. In other words, the release mechanism 1808 may allow a single motion to lock or release the headrest 116 along multiple axis of movement.

Figure 19:
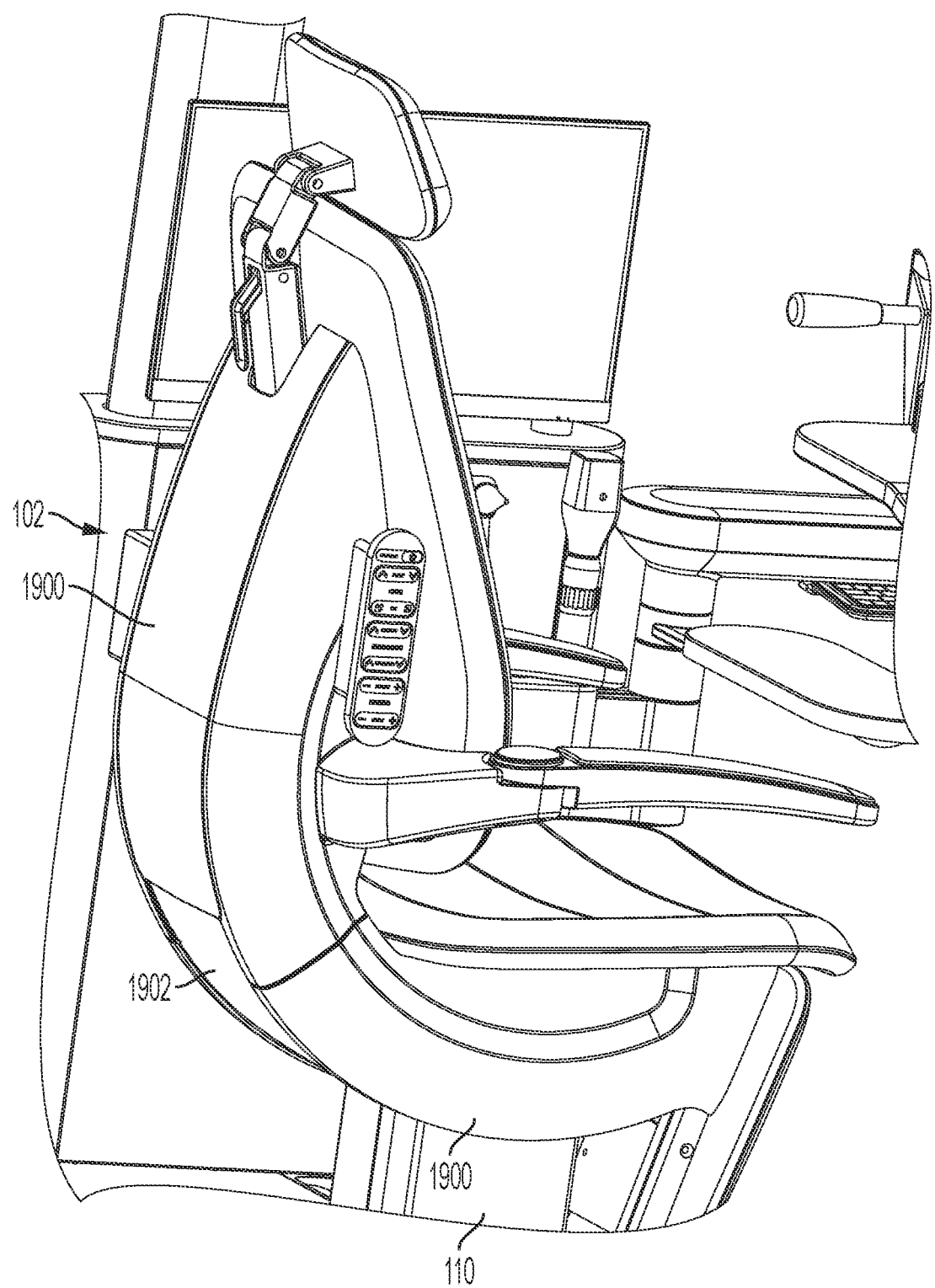
FIG. 19 is a partial perspective view of a patient chair.

Referring now to FIG. 19, yet another aspect of this disclosure is the ability of the patient chair 102 to tilt and position any patient therein in an advantageous orientation for the professional. The patient chair 102 may generally have paneling 1900 around the inner portions of the patient chair 102 that are not typically occupied by a patient. The paneling 1900 may both protect the patient and professional from being injured by the moving components of the patient chair 102 and protect the moving components of the patient chair 102 from debris and other environmental factors that may affect the moving components. Accordingly, the paneling 1900 may separate the moving components from the surrounding environment.

The patient chair 102 may have a sliding shield 1902 defined along a portion of the patient chair 102 that is proximate to the pedestal 110. The sliding shield 1902 may be slidably coupled to other portions of the paneling 1900 to allow the patient chair 102 to pivot between a tilted position and an upright position without exposing the moving components of the patient chair 102 to the surrounding environment. The sliding shield 1902 may slightly overlap an internal portion of the paneling 1900 on one end and be coupled to the pedestal 110 on the other. As the patient chair 102 pivots from the upright position to the tilted position, the sliding shield 1902 may slide further into the paneling 1900 to provide a greater overlap while continuing to protect the moving components from the surround environment. Alternatively, as the patient chair 102 transitions from the tilted position to the upright position, the overlap between the sliding shield and the paneling 1900 may be reduced while continuing to protect the moving components from the surrounding environment. In other words, the paneling 1900 and sliding shield 1902 may correspond with one another to allow the patient chair 102 to transition between the tilted position and the upright position without exposing the moving components to the surrounding environment.

This disclosure considers generating the integrated medical equipment 100 to substantially hide all wiring within cavities of the components described herein. Accordingly, in one aspect of this disclosure there may be only a single power chord or outlet on the integrated medical equipment that requires power from an external source before every medical device on the equipment 100 is powered. Further, this disclosure achieves the overall hidden wire look by routing wires through pivot axes of articulating components of the equipment 100 to ensure that minimal wire length is needed to accommodate all of the devices and the wires are routed through locations that will generate minimal wear on the wires.

In yet another aspect of this disclosure, any of the arms 128, 150, 168 or other components of the equipment 100 may be electrically repositionable utilizing motors, actuators, and the like. More specifically, the medical device arm 132 may be raised and lowered in the direction 134 through an actuator positioned between the slide 1502 and the rail 1504. The actuator may be selectively repositioned based on input from any of the controllers 180, 182, 240 described herein. Alternatively, a controller for repositioning the actuators may be remotely controlled through an app on a remote device such as a tablet, smartphone, or other computing device. The platform support arm 150 may similarly have an actuator positioned between the support arm 150 and the housing 165 to allow the platforms 154, 156 to be selectively repositioned via the actuator and any of the controllers described herein.

In another aspect of this disclosure, any of the articulating components of the equipment 100 may have home or preset positions as described for the platforms 154, 156. For example, the illumination arm 128 may have preset positions wherein the segments 1702 are aligned relative to one another and the illumination arm 128 is rotationally positioned about the vertical light axis 1706 to be positioned substantially over the housing 165. In this configuration, detents, stops, or the like may be positioned along any of the axis 1704, 1706 to provide an increased resistance to movement of the illumination arm 128 once it is in the home or other preset position.

The second arm 138 may similarly have a preset position about the arm axis 1506 utilizing any of the methods described herein. The preset position may be when the second arm 138 is aligned with a plane substantially in front of a seated patient. Similarly, the sliding motion of the inner second arm 138b relative to the outer second arm 138a may have a home position wherein the force required to slide the inner second arm 138b is increased relative to sliding the arm 138b at other locations. In this example, the home position may be a location along the second direction 1508 that substantially centers any device coupled to the inner second arm 138b to the patient chair 102.

In yet another aspect of this disclosure, the patient chair 102 may be pivotally coupled to the pedestal 110 with an actuator or the like. In this configuration, the pedestal 110 may telescopically raise or lower the patient chair while the actuator may selectively tilt the seat 112, back 114, calf support 122, and footrest 123 as substantially one tilting unit.

The terminology used herein is for the purpose of describing particular illustrative embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations).

While exemplary embodiments incorporating the principles of the present disclosure have been disclosed herein, the present disclosure is not limited to the disclosed embodiments. Instead, this application is intended to cover any variations, uses, or adaptations of the disclosure using its general principles. Further, this application is intended to cover such departures from the present disclosure as come within known or customary practice in the art to which this invention pertains.

What is claimed is:

1. An integrated medical equipment for supporting medical equipment and a patient during a medical procedure, the integrated medical equipment comprising:
   a base;
   an adjustable chair operatively connected to the base;
   an equipment support operatively connected to the base and spaced from the adjustable chair by a predetermined distance, wherein the equipment support includes a column at the base and a tower extending generally vertically from the column;
   a medical device arm operatively connected to the tower, wherein the medical device arm is motor driven to move along the generally vertical tower;
   a platform support arm operatively connected to the column, wherein the platform support arm is motor driven to move generally vertically along the column; and
   a monitor arm pivotably coupled to the equipment support, wherein the monitor arm includes a monitor coupler to couple a monitor to the monitor arm.

2. The integrated medical equipment of claim 1 wherein the monitor arm includes an access port to allow one or more cables to be operatively connected to the monitor.

3. The integrated medical equipment of claim 2 wherein the tower includes a rail and the medical device arm includes a terminating end operatively connected to the rail, such that the terminating end moves vertically along the tower.

4. The integrated medical equipment of claim 3 wherein the medical device arm include a first arm having the terminating end and a second arm pivotally coupled to the first arm, wherein the second arm includes an outer second arm and in inner second arm, wherein the inner second arm slides along the outer second arm and includes a coupler to support a phoropter.

5. The integrated medical equipment of claim 4 further comprising a slide disposed at the rail and operatively connected to the medical device arm, wherein the slide moves with the medical device arm during movement along the tower.

6. The integrated medical equipment of claim 5 wherein the medical device arm includes a handle operatively connected to the inner second arm to move the phoropter.

7. The integrated medical equipment of claim 6 wherein the platform support arm rotatably supports a first platform and rotatably supports a second platform disposed beneath the first platform, wherein the first platform and the second platform are separately rotatable.

8. The integrated medical equipment of claim 7 wherein the first platform includes rotatable support supported by a moveable support, wherein the movable support moves longitudinally along a length of the first platform, and the rotatable support rotates with respect to the movable support, the rotatable support including a flange to couple to an equipment tray.

9. The integrated medical equipment of claim 8 wherein the flange includes a hollow passage to provide a wire routing location.

10. The integrated medical equipment of claim 9 further comprising a keyboard tray and a swivel connector, wherein the second platform supports the swivel connector to provide for rotation of the keyboard tray with respect to the second platform.

11. The integrated medical equipment of claim 10 wherein the equipment tray includes an extension defining a cavity to receive a handheld remote controller.

12. The integrated medical equipment of claim 11 wherein the chair includes a leg rest having a stop, a calf support, and a footrest extending from the leg rest, wherein the stop prevents rotation of the footrest with the calf support such that the footrest remains at a relatively flat position with respect to a plane of a floor upon which the base sits.

13. The integrated medical equipment of claim 12 further comprising an illumination arm supported by the tower, wherein the illumination arm is rotatably supported by the tower and includes an examination light and segments located between the examination light and the tower, the segments being positionable to adjust the position of the examination light.

14. An integrated medical equipment for supporting medical equipment a patient during a medical procedure, the integrated medical equipment comprising:
   a base;
   a chair operatively connected to the base, the chair including an adjustable pedestal to raise and lower the chair;
   an equipment support operatively connected to the base and spaced from the adjustable chair by a predetermined distance, wherein the equipment support includes a column at the base and a tower extending generally vertically from the column;
   a medical device arm operatively connected to the tower, wherein the medical device arm is motor driven to move along the generally vertical tower and supports a phoropter;
   a platform support arm operatively connected to the column, wherein the platform support is motor driven to move generally vertically along the column and supports a slit lamp;

a monitor supported by the column; and a hand held remote controller operatively connected to the chair, the medical device arm, the phoropter, the slit lamp, and the monitor, wherein the remote controller controls a position of the chair, a position of the medical device arm, and operation of the phoropter, the slit lamp, and the monitor.

15. The integrated medical equipment of claim 14 further comprising an illumination arm supported by the tower, wherein the illumination arm is rotatably supported by the tower and includes an examination light and segments located between the examination light and the tower, the segments being positionable to adjust the position of the examination light.

16. The integrated medical equipment of claim 15 wherein the remote controller controls lighting of the examination light.

17. The integrated medical equipment of claim 16 wherein the tower includes a rail and the medical device arm includes a terminating end operatively connected to the rail, such that the terminating end moves vertically along the tower.

18. The integrated medical equipment of claim 17 wherein the medical device arm includes a first arm having the terminating end and a second arm pivotably coupled to the first arm, wherein the second arm includes an outer second arm and in inner second arm, wherein the inner second arm slides along the outer second arm and includes a coupler to support a phoropter.

19. The integrated medical equipment of claim 18 wherein the first platform rotatably supports an equipment tray equipment including an extension defining a cavity to receive a remote controller.

* * * * *